United States Patent
Christiansen et al.

(10) Patent No.: US 11,691,011 B2
(45) Date of Patent: Jul. 4, 2023

(54) PAIN-RELIEVING APPARATUS

(71) Applicant: Black Diamond Creations, LLC, St. George, UT (US)

(72) Inventors: Brett D. Christiansen, St. George, UT (US); Christopher B. Christiansen, St. George, UT (US); James B. Christiansen, St. George, UT (US); Clancy B. Christiansen, St. George, UT (US); Candice S. Christiansen, St. George, UT (US); Bryce B. Christiansen, St. George, UT (US); Susan G. Christiansen, St. George, UT (US); Phillip Dietz, St. George, UT (US)

(73) Assignee: Black Diamond Creations, LLC, St. George, UT (US)

(*) Notice: Subject to any disclaimer, the term of this patent is extended or adjusted under 35 U.S.C. 154(b) by 331 days.

(21) Appl. No.: 16/874,584

(22) Filed: May 14, 2020

(65) Prior Publication Data
US 2020/0360691 A1    Nov. 19, 2020

Related U.S. Application Data

(60) Provisional application No. 62/848,220, filed on May 15, 2019.

(51) Int. Cl.
*A61N 1/36*    (2006.01)
*A61H 9/00*    (2006.01)
(Continued)

(52) U.S. Cl.
CPC .......... *A61N 1/36021* (2013.01); *A61H 1/00* (2013.01); *A61H 9/0057* (2013.01);
(Continued)

(58) Field of Classification Search
CPC .............. A61N 1/36021; A61N 1/0456; A61N 1/0492; A61N 1/37247; A61H 1/00; A61H 2201/0207; A61H 2201/0214; A61H 2201/105; A61H 2201/501; A61H 2201/5048; A61H 2201/5097; A61H 2201/1207; A61H 2201/1253; A61H 2201/169; A61H 2201/1695;
(Continued)

(56) References Cited

U.S. PATENT DOCUMENTS 6,546,290 B1 * 4/2003 Shloznikov ........ A61N 1/36021
                                                    607/46
10,406,358 B1 * 9/2019 Bertoch .................. A61N 1/325
(Continued)

*Primary Examiner* — Justine R Yu
*Assistant Examiner* — Kelsey E Baller
(74) *Attorney, Agent, or Firm* — Gurr Brande & Spendlove, PLLC; Robert A. Gurr

(57) ABSTRACT

The pain-relieving apparatus has a housing, a stimulating surface, user inputs, and a plurality of ports, such as a battery port and a transcutaneous electrical nerve stimulation (TENS) output connector. The stimulating surface may include a suction ring, vacuum apertures, vibration stimulators, a plate, heat and cold transducer elements, and
(Continued)

medicinal holders to provide various approaches for relieving pain. The pain-relieving apparatus may also have a sound speaker for producing nerve stimulating sounds.

4 Claims, 16 Drawing Sheets

(51) Int. Cl.
    *A61H 1/00*           (2006.01)
    *A61K 9/70*           (2006.01)
    *A61K 31/167*       (2006.01)

(52) U.S. Cl.
CPC .......... *A61K 9/7007* (2013.01); *A61K 31/167* (2013.01); *A61H 2201/0207* (2013.01); *A61H 2201/0214* (2013.01); *A61H 2201/105* (2013.01); *A61H 2201/501* (2013.01); *A61H 2201/5048* (2013.01); *A61H 2201/5097* (2013.01)

(58) Field of Classification Search
CPC .... A61H 2201/0221; A61H 2201/5023; A61H 2201/5025; A61H 23/0263; A61H 23/008; A61H 23/0245; A61H 9/0057; A61K 9/7007; A61K 31/167; A61M 35/00
See application file for complete search history.

(56) References Cited

U.S. PATENT DOCUMENTS

| | | | |
|---|---|---|---|
| 10,589,116 B1* | 3/2020 | Yu | A61H 23/0218 |
| 10,682,508 B1* | 6/2020 | Theriot | A61K 47/10 |
| 2005/0043655 A1* | 2/2005 | Schenck | A61N 1/321 601/71 |
| 2007/0282400 A1* | 12/2007 | Gorham | A61N 5/0616 607/151 |
| 2008/0215039 A1* | 9/2008 | Slatkine | A61M 5/425 606/9 |
| 2012/0046579 A1* | 2/2012 | Radi | A61H 11/00 601/46 |
| 2015/0283022 A1* | 10/2015 | Lee | A61H 7/00 601/2 |
| 2017/0196757 A1* | 7/2017 | Palomaki | A61H 9/0057 |
| 2018/0326205 A1* | 11/2018 | Cheng | A61N 1/36021 |
| 2018/0369064 A1* | 12/2018 | Baxter | A61F 7/02 |
| 2020/0188663 A1* | 6/2020 | Nachum | A61N 1/36034 |
| 2020/0289813 A1* | 9/2020 | Ito | A61N 1/0452 |
| 2020/0368518 A1* | 11/2020 | Vera-Portocarrero | A61N 1/37211 |
| 2022/0096312 A1* | 3/2022 | Liu | A61H 23/00 |

* cited by examiner

PAIN-RELIEVING APPARATUS

CROSS-REFERENCE TO RELATED APPLICATIONS

This application claims the benefit of U.S. Provisional Application Ser. No. 62/848,220, filed on May 15, 2019, which is incorporated herein by reference.

TECHNICAL FIELD

The present disclosure relates to pain relieving devices. More particularly, the present disclosure relates to a pain-relieving apparatus that decreases and/or eliminates pain signals traveling to the brain by using a combination of cooling, heating, vibration, suction, TENS, lidocaine, sound, and video.

BACKGROUND

Since 2016, the opioid crisis in the USA has been responsible for an estimated 50,000 to 72,000 deaths annually due to overdose. This has grown from an estimated 12,000 to 50,000 annual deaths since 2002. This is especially a problem within the United States. In particular, an astounding 80% of the world's pharmaceutical supply is consumed by the U.S. each year. With few alternatives to treating chronic pain, there will continue to be pain-relieving medication abuse and addiction.

The dependence on opioids and other pain-relieving medications have led to several non-medicinal approaches for relieving pain that exist in the art. These approaches use acupuncture, electrical nerve stimulation, heating and cooling devices, vibrational devices, and other methods. However, the plethora of devices, and their unique approaches to pain reduction, make it difficult and expensive to effectively treat pain. In other words, a user may end up paying for several approaches until the preferred approach is discovered. For example, a single approach may use heating and cooling without utilizing the other pain-reducing approaches. This one-dimensional approach to pain relief creates difficulty when addressing chronic pain, because individuals may require unique stimuli, in different forms, that will be optimal for their nerve and sensation needs. Trying to find which stimulation works for them is expensive and time-consuming, which leads to the continued reliance on medication.

Further, after receiving a prescription from a doctor, pain-relieving medication can be easily obtained. In the end, the pain-relieving medication may cause more harm than help, making an individual dependent on medication and, ultimately, addicted. Not only can those that have chronic pain abuse the pain-relieving medication, but youth, or other individuals that live in the same house, may abuse it. In addition, it is felt that combining different modalities together into one device might have an additive effect that will significantly decrease the pain that an individual feels, not only leading to the decreased use of pain medications as well as the ability to use lower amounts of heat, vibration, suction or electrical stimulation used individually.

Accordingly, there is a need to reduce the dependence on opioids and other pain-relieving medications by using a pain-relieving apparatus with multiple functionalities and approaches to pain relief, that is compact, and that is inexpensive. The present disclosure seeks to solve these and other problems.

SUMMARY OF EXAMPLE EMBODIMENTS

In one embodiment, the pain-relieving apparatus comprises a housing, a stimulating surface, user inputs, and a plurality of ports, such as a battery port and a transcutaneous electrical nerve stimulation ("TENS") output connector. The stimulating surface may comprise a suction ring, vacuum apertures, vibration stimulators, a plate, and medicinal holders to provide various approaches for relieving pain. The pain-relieving apparatus may further comprise a sound speaker for producing nerve stimulating sounds. In one embodiment, the pain-relieving apparatus comprises user inputs through a smartphone application. The smartphone has additional sound and video options for distraction from pain.

In one embodiment, a method of using the pain-relieving apparatus comprises a user placing the pain-relieving apparatus on a painful area of the body via attachment sites. Through user inputs, whether on a smartphone or on the pain-relieving apparatus, the user selects which type of pain control modality to use. The user may use multiple modalities at the same time. The user adjusts the intensity of each modality of pain control from the user inputs. By varying between modalities and intensities, the user is able to find the pain control modality(ies) that best treat the pain. For example, the user may select plate and vacuum apertures to provide heat/cold, vibration, and suction, respectively. The user then determines if the pain control modalities distract the pain stimulus and provide relief. If the modalities do not provide relief, then the user selects other modalities to use, alone or together, to determine the best pain relief option.

In one embodiment, a pain-relieving apparatus comprises a housing, a removably attachable cooling component, user inputs, and medicinal holders. In an alternate embodiment, the pain-relieving apparatus may be a single unit with all components.

DETAILED DESCRIPTION OF EXAMPLE EMBODIMENTS

Figure 1:
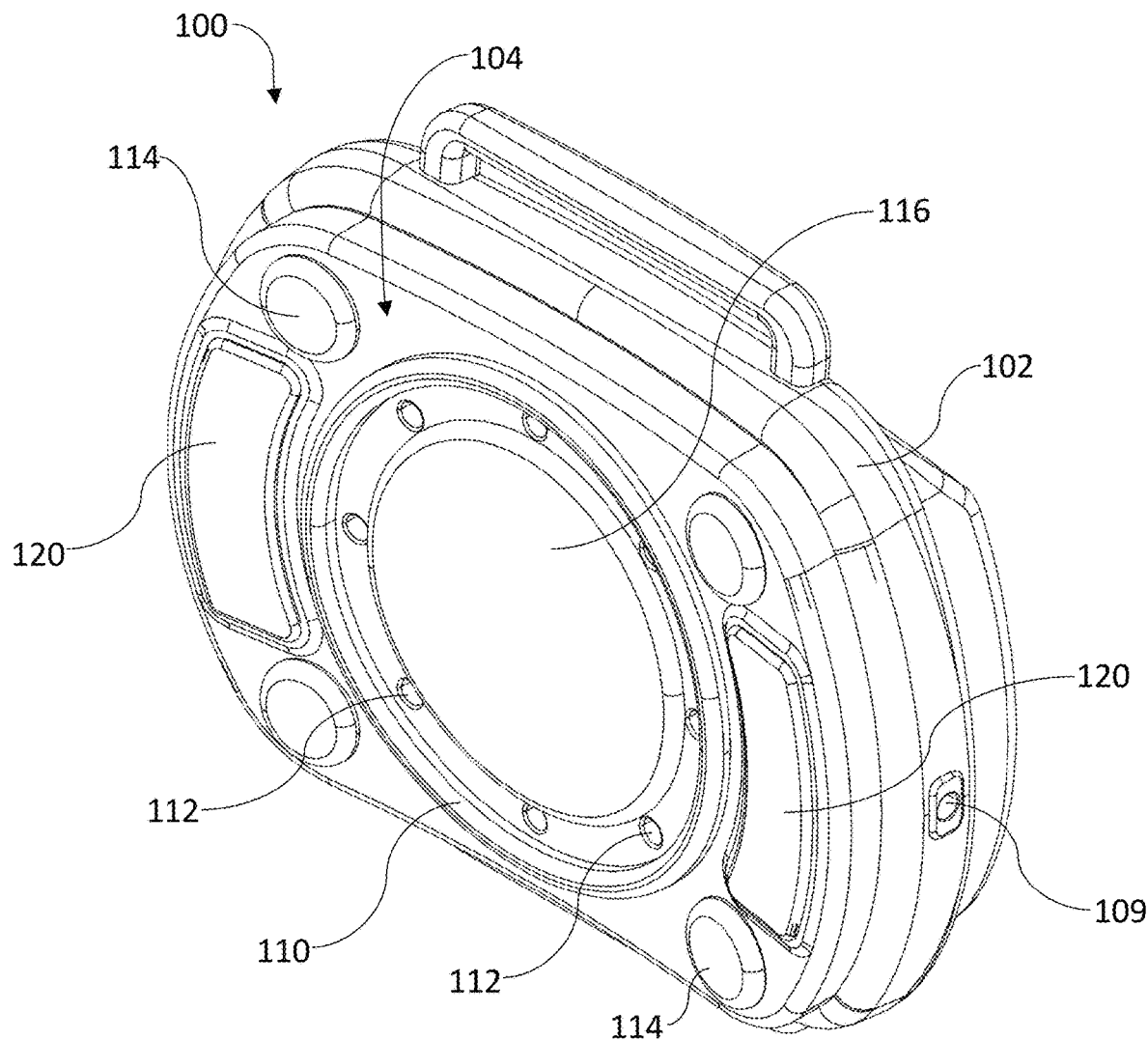
FIG. 1 illustrates a bottom, rear perspective view of a pain-relieving apparatus.

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbesuction ring patterns from one embodiment to the other need not imply that each embodiment has similar parts, although it may.

Accordingly, the particular arrangements disclosed are meant to be illustrative only and not limiting as to the scope of the invention, which is to be given the full breadth of the appended claims and any and all equivalents thereof. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.).

As previously discussed, there is a need for a pain-relieving apparatus with multiple functionalities and approaches to pain relief, that is compact, inexpensive, and that reduces dependence on medications. The pain-relieving apparatus disclosed herein solves these problems and others.

In general, the pain-relieving apparatus disclosed herein comprises numerous pain relief modalities to decrease and/or eliminate pain. Typically, a user is limited to addressing pain through one or two pain relief modalities, such as heat and cold, or through consuming pain-relieving medication, which may lead to abuse and addiction. In contrast, the pain-relieving apparatus herein may include numerous pain relief modalities to address a user's particular pain in a customizable manner. For example, the pain-relieving apparatus may utilize vibration, cooling, heating, suction, TENS, lidocaine, video, and sound to overload nerve pathways to eliminate pain signals. A user is able to select the pain relief modality that best addresses the pain that is being experienced. That is, the user is able to combine numerous pain relief modalities, at varying levels of intensity, to prevent nerves from sending pain signals to the brain.

In particular, the pain-relieving apparatus is capable of stimulating the projection neuron. Nerves transmit sensory stimuli to the "projection neuron," which is referred to as signaling. This signaling works well to transmit a single sensory projection. With chronic pain, this neuron is transmitting the signal of pain constantly to the brain. The prior art contains some nerve stimulating mechanisms that interact with the projection neuron. However, the prior art devices have used a combination of only one or two pain control modalities to combat pain, which the efficacy of such devices ranges as many individuals require unique stimuli that is optimal for their nerve and sensation needs. Accordingly, these devices fail to adequately control the user's personalized pain by being limited to using one or two modalities, which forces many users to consume pain-relieving medication. In contrast, the pain-relieving apparatus disclosed herein contains numerous pain control modalities to combat pain, which create a personalized pain relief system for any user and allows for maximum pain relief. Moreover, the user is able to find the right combination for any pain, allowing the user to use the pain-relieving apparatus instead of relying on pain-relieving medication.

Figure 2:
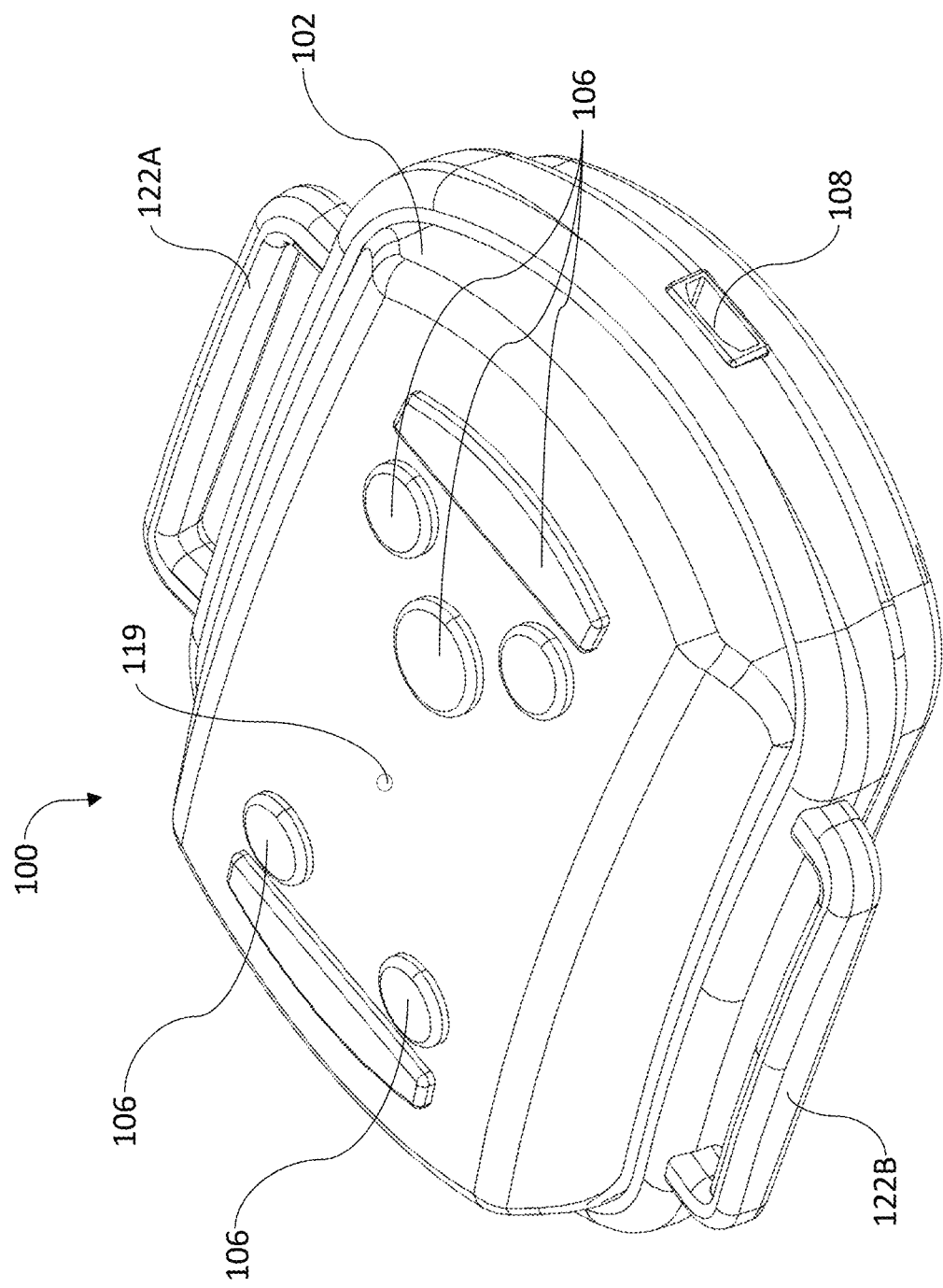
FIG. 2 illustrates a top, front perspective view of a pain-relieving apparatus.

In one embodiment, as shown in FIGS. 1-2, the pain-relieving apparatus 100 comprises a housing 102, a stimulating surface 104, user inputs 106, and one or more ports, such as a battery port 108 and a TENS output connector 109. The pain-relieving apparatus 100 may vary in size and shape. For example, the housing 102 may be compact for traveling or larger for at home or institutional use. The housing 102, as shown, may be oval shaped. However, the housing 102 may be other formfactors, such as circular, square, hourglass, etc.

The stimulating surface 104 may comprise a variety of pain control modalities, such as a suction ring 110, vacuum apertures 112, vibration stimulators 114, a plate 116, and medicinal holders 120. While the stimulating surface 104 may comprise numerous pain control modalities, as mentioned above, it will be appreciated that the pain-relieving apparatus 100 can have many, or few, pain control modalities, as well as different types of pain control modalities. For example, in some embodiments, the stimulating surface may be limited to the vibration stimulators 114 and the plate 116. In other words, any variety of modalities may be combined into a single unit.

Figure 3:
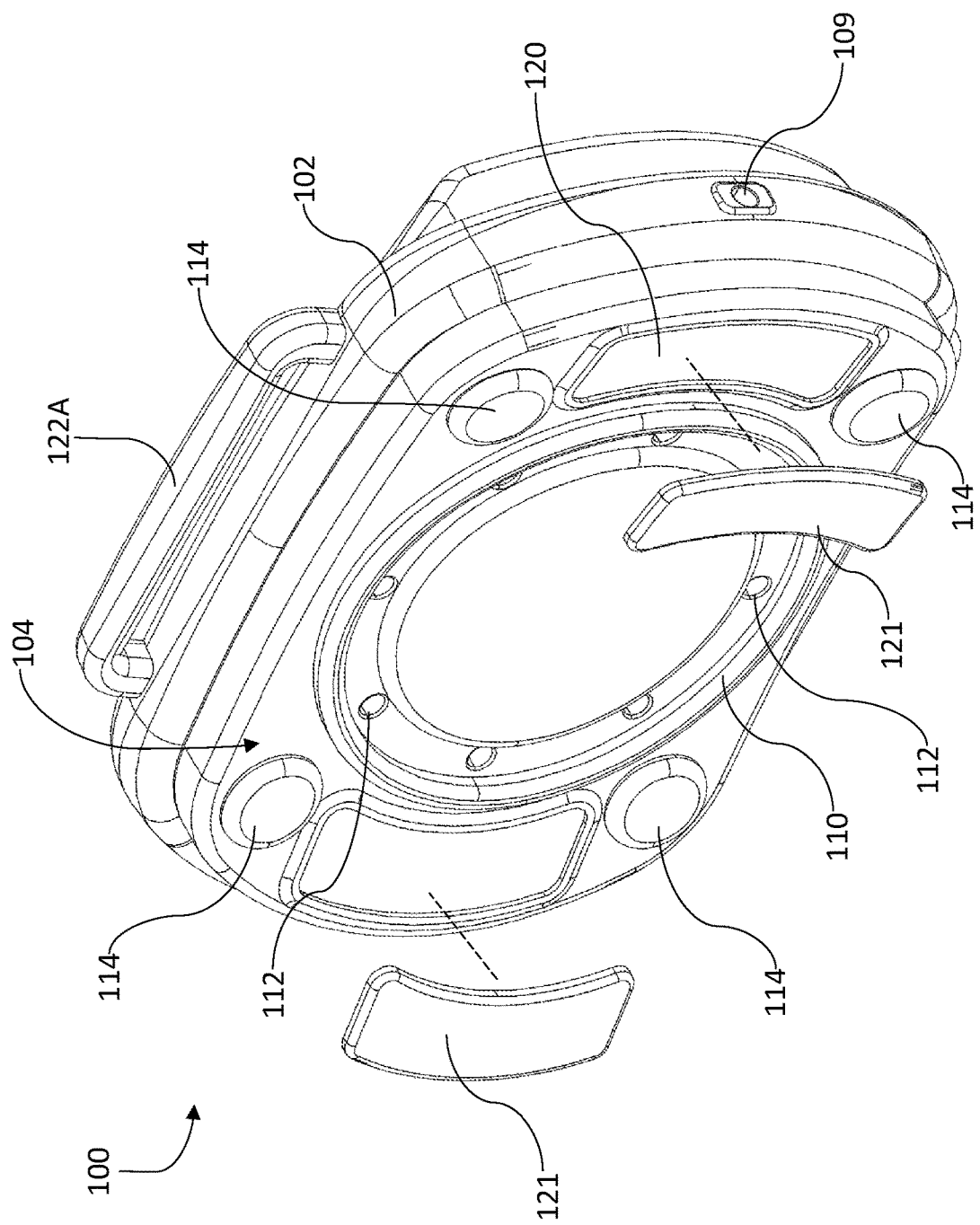
FIG. 3 illustrates a bottom, rear perspective view of a pain-relieving apparatus with lidocaine patches decoupled therefrom.
Figure 4:
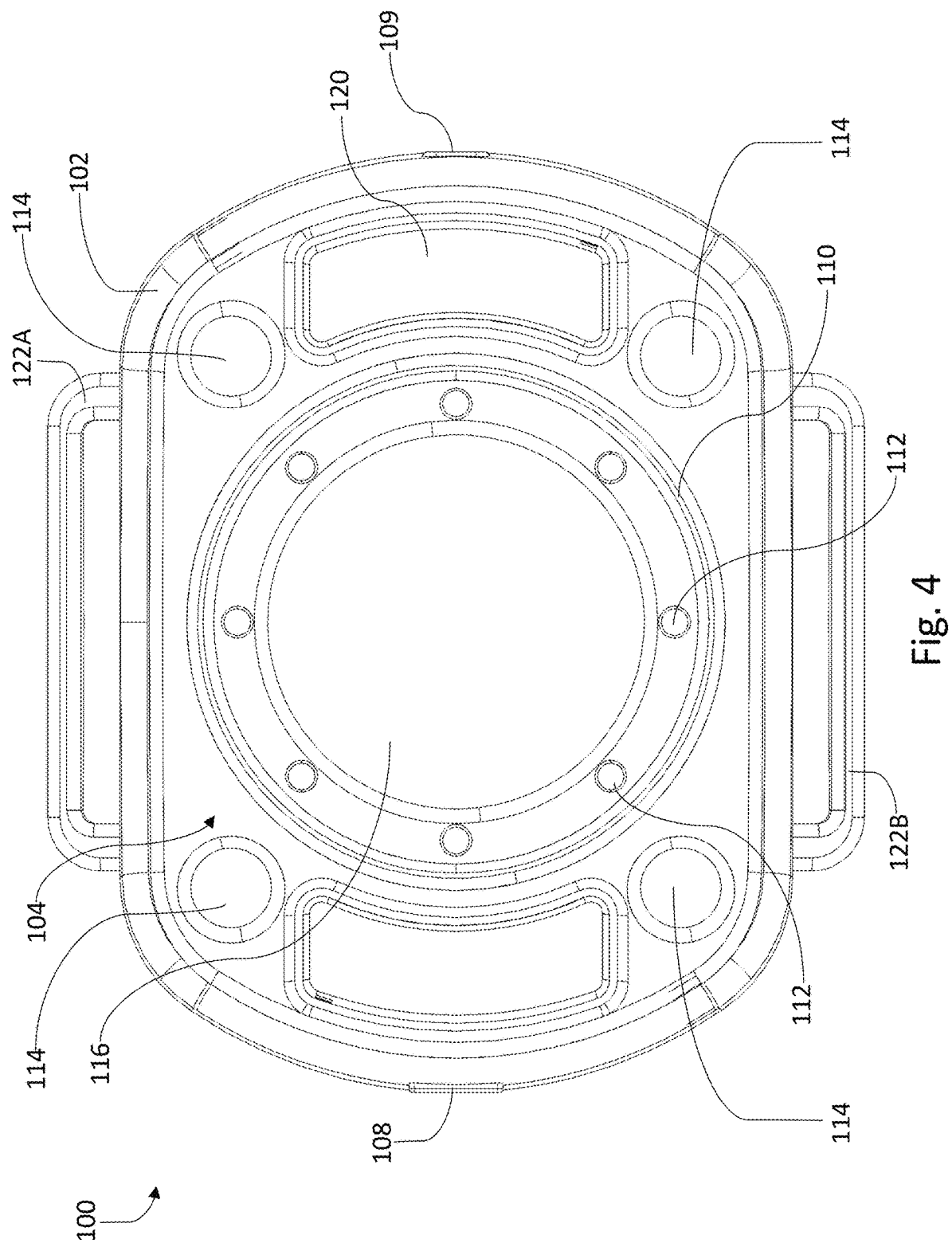
FIG. 4 illustrates a bottom plan view of a pain-relieving apparatus.
Figure 5:
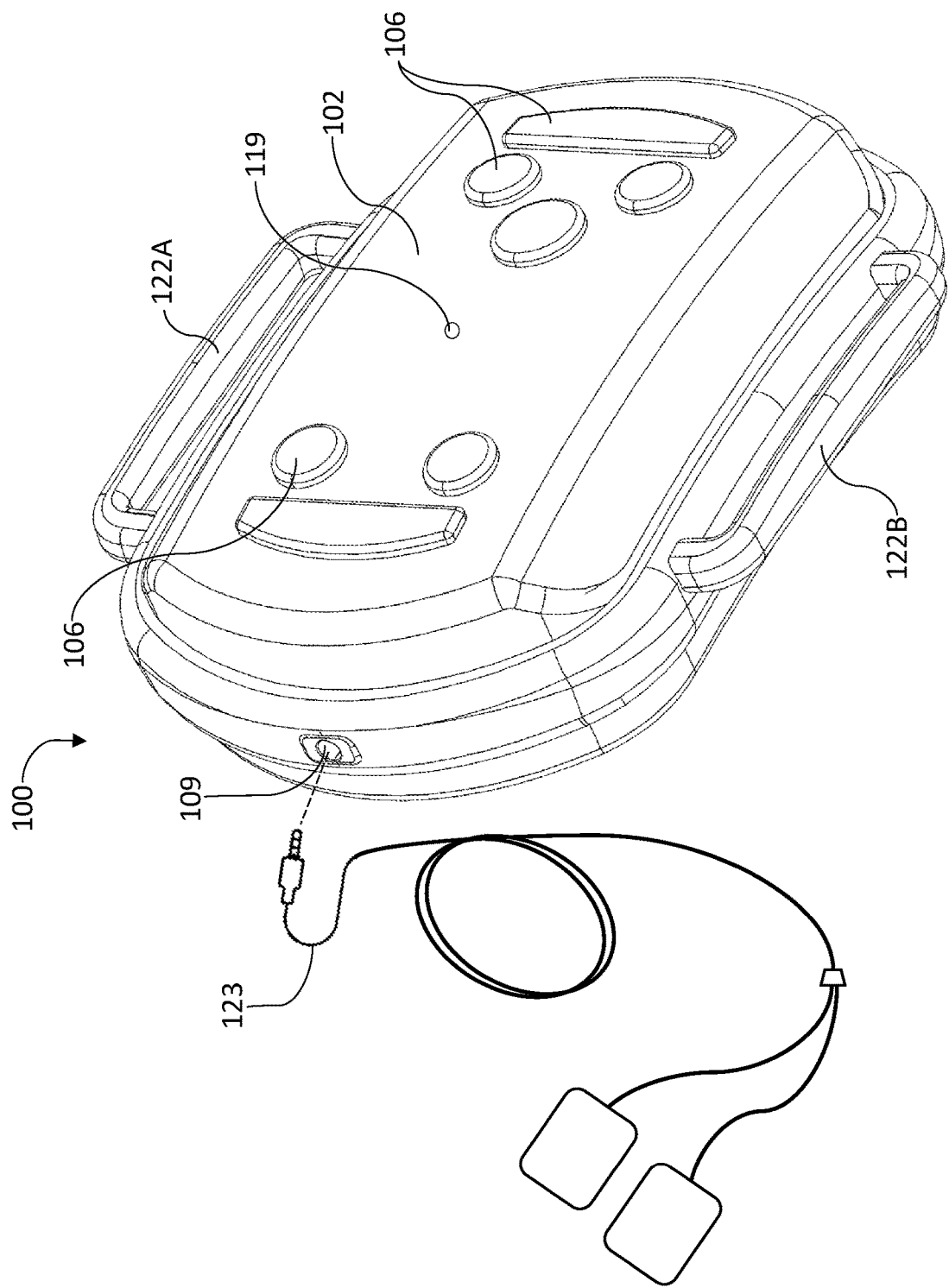
FIG. 5 illustrates a top, rear perspective view of a pain-relieving apparatus with a TENS cable.

Referring to FIGS. 3-5, the suction ring 110 segregates the various types of pain control modalities. Further, the suction ring 110 may be an elastomer suction ring that seals to the user so as to assist in suction therapy through the vacuum apertures 112. While a circular suction ring may be shown, other shapes may be used to create a seal, such as an oval. After the suction ring 110 is sealed to a user, the vacuum apertures 112 produce nerve stimuli that distracts the pain signaling stimuli. The vacuum apertures 112 may be evenly spaced in a circular formation within the suction ring 110, as shown, or in any other formation, such as a linear formation, patterned, scattered, etc. It will be appreciated that the vacuum apertures 112 may vary in diameter as well. It will further be appreciated that the intensity of the suction from the vacuum apertures 112 may vary. In an alternate embodiment, the pain-relieving apparatus comprises a single vacuum aperture to provide suction therapy. The suction may be a continuous suction or vary between off and on in various frequencies to change the relief from pain.

As the suction ring 110 can provide a seal for suction therapy, a plate 116 (best shown in FIGS. 1 and 3-4) can provide pain relief through heating or cooling. The plate 116, for example, can be located within the suction ring 110 so that a user can experience suction therapy through the vacuum apertures 112 and heating or cooling simultaneously, which may allow a user's pain to be distracted by multiple pain-relieving modalities. In addition, the vibration stimulators 114 on the stimulating surface 104 may be made from many materials, such as rubber, plastic, or metal. Further, in one embodiment, the vibration stimulators 114 may comprise at least one plate that vibrates and provides heat and cold. While a plurality of vibration stimulators 114 are shown, it will be appreciated it can be as few as one vibration stimulator.

Further, a sound speaker 119 and medicinal holders 120 assist a user by using a different pain relief modality. As a user may experience heat, vibration, and suction, the user can also experience nerve stimulation through sounds and medicine placed on medicinal holders 120. The sound speaker 119 produces sound to stimulate auditory processing and reduce the effect of pain signals to the brain. Various sounds, such as ringing, beeping, or therapeutic music, may be used at a variety of frequencies. Alternatively, the sound may be transmitted from a phone 124 used to control the device via a phone speaker 117 (shown in FIG. 6). While the sound speaker 119 may be used for auditory stimulation, it will be appreciated that sound may also be used for shockwave therapy or ultrasound therapy for controlling pain. The medicinal holders 120 can accept removably attachable medicinal patches 121, such as lidocaine patches, to further stimulate the desired nerve. It will be appreciated that other types of local anesthetic may be used in place of lidocaine, such as anesthetic from the ester group (e.g., procaine or benzocaine). All of the pain control modalities can be turned on and off independent of the others as well as adjusted for intensity for unique combinations that provide customizable relief for a user. For example, the user may increase temperature on the plate 116 and have the vibration stimulators 114 at a low frequency to address the user's unique pain.

Referring to FIG. 5, the user inputs 106 may be push buttons; however, it will be appreciated that the user inputs 106 may be knobs, dials, a touch screen, or any other inputting device known in the art. The user actuates the user inputs 106 to control which pain control modality is activated and its intensity, such as vibration at low level. For example, to vary intensity, buttons may be pressed in succession or dials turned, etc. The pain-relieving apparatus 100 operates from a battery which is charged through a battery charging port 108 (shown in FIG. 2), such as a USB port, micro USB port, or AC port. Other charging ports or a charging device known in the art may be used, such as a wireless charging dock. With the use of batteries that can be rechargeable, the user is able to easily carry and operate the pain-relieving apparatus 100 in any location.

A pain-relieving apparatus 100 further comprises the TENS output connector 109. The TENS output connector 109 may be located on the housing 102. The TENS output connector 109 sends small electrical impulses into a painful area of a user via TENS cables 123. The TENS output connector 109, with the TENS cables 123, helps the body produce natural pain relief, often in the form of endorphins. A pain-relieving apparatus 100 further comprises attachment sites 122A, 122B. The attachment sites 122A, 122B allow the pain-relieving apparatus 100 to be coupled to a user by using woven straps, elastic bands, hook and loop straps, or other attachment means.

Figure 6:
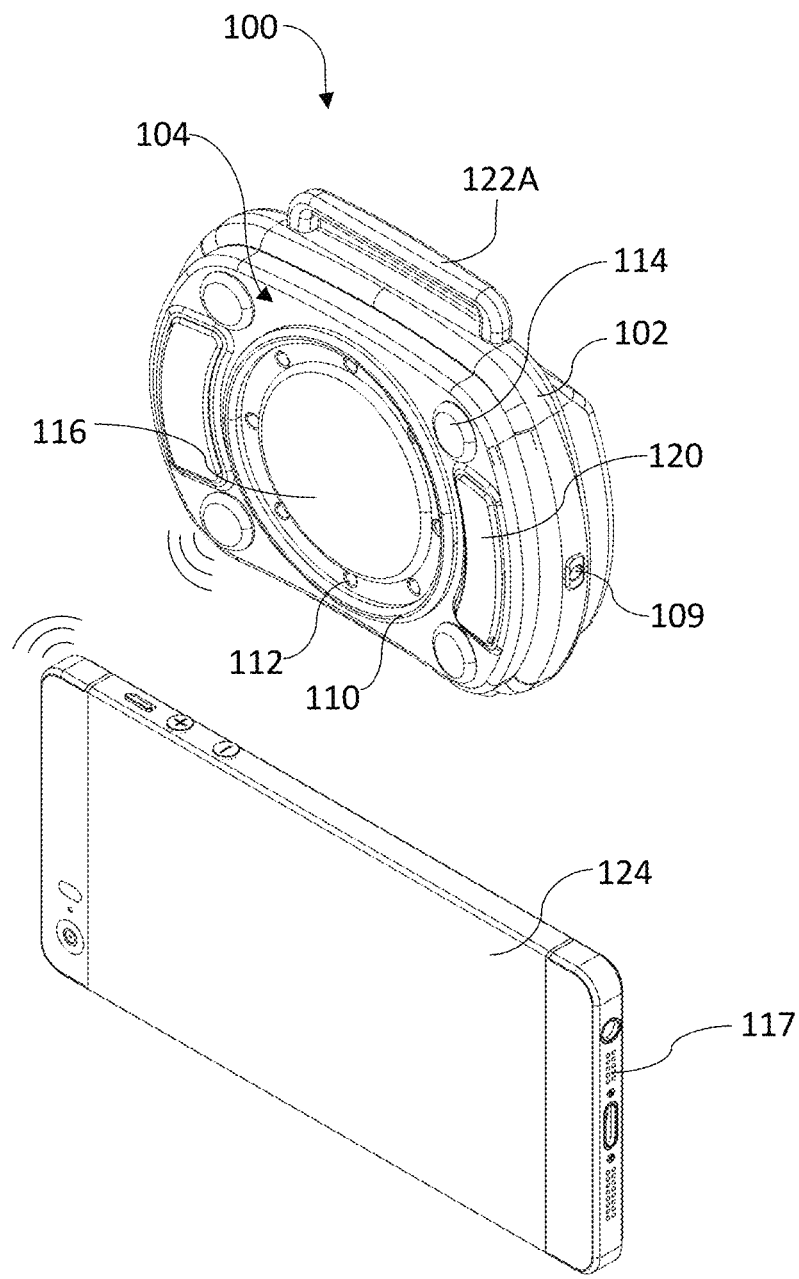
FIG. 6 illustrates a bottom, rear perspective view of a pain-relieving apparatus with a smartphone.
Figure 7:
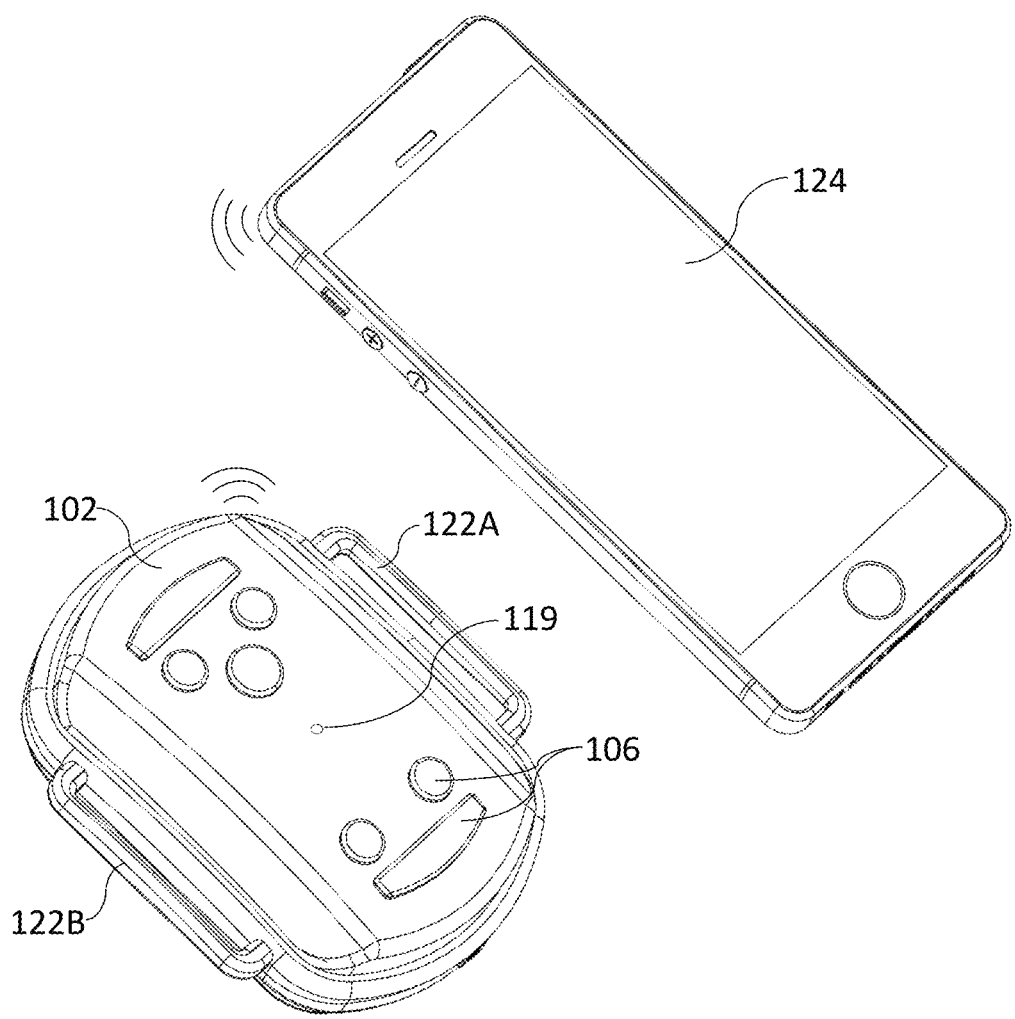
FIG. 7 illustrates a top perspective view of a pain-relieving apparatus with a smartphone.
Figure 8:
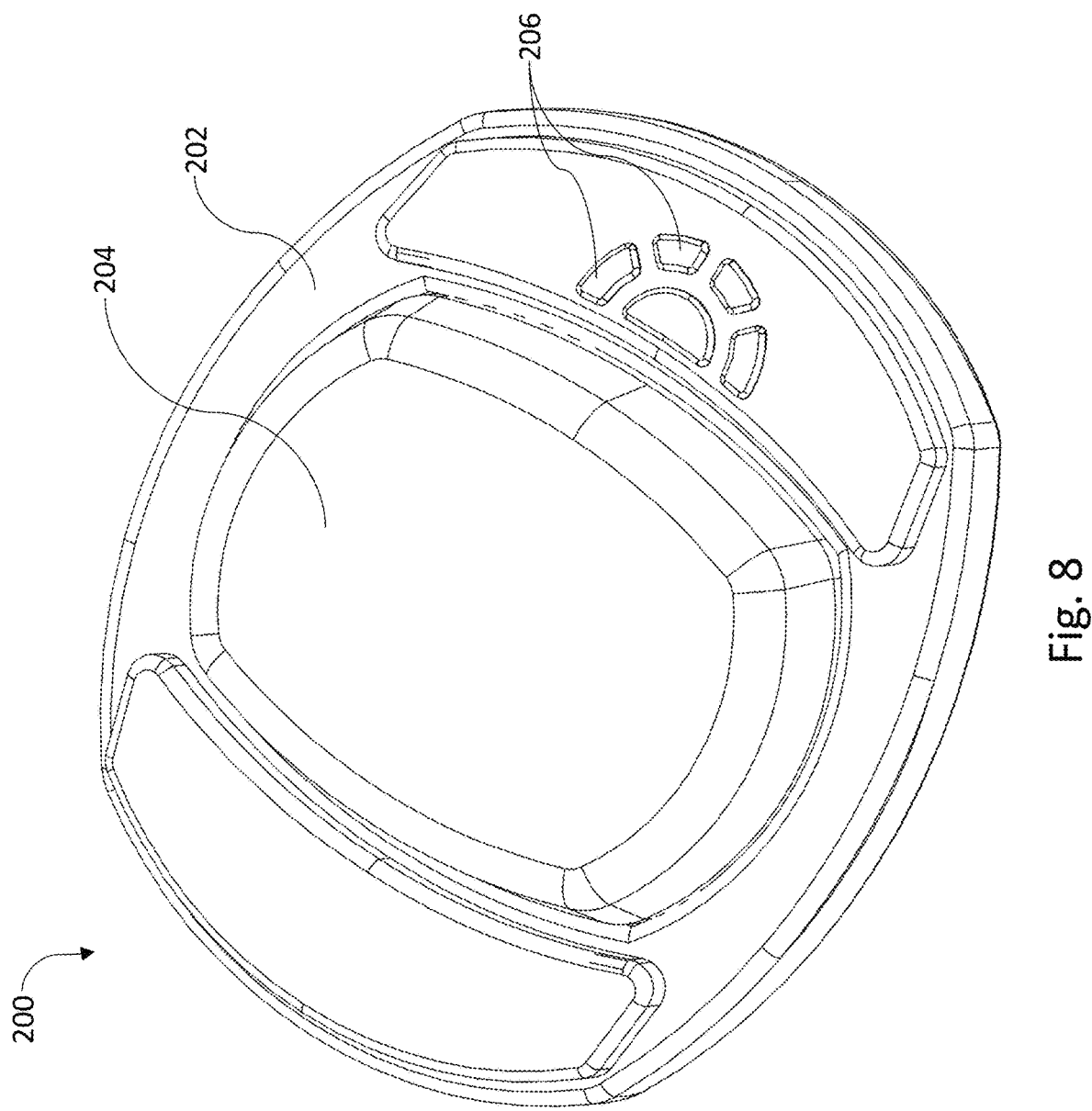
FIG. 8 illustrates a top perspective view of a pain-relieving apparatus.
Figure 9:
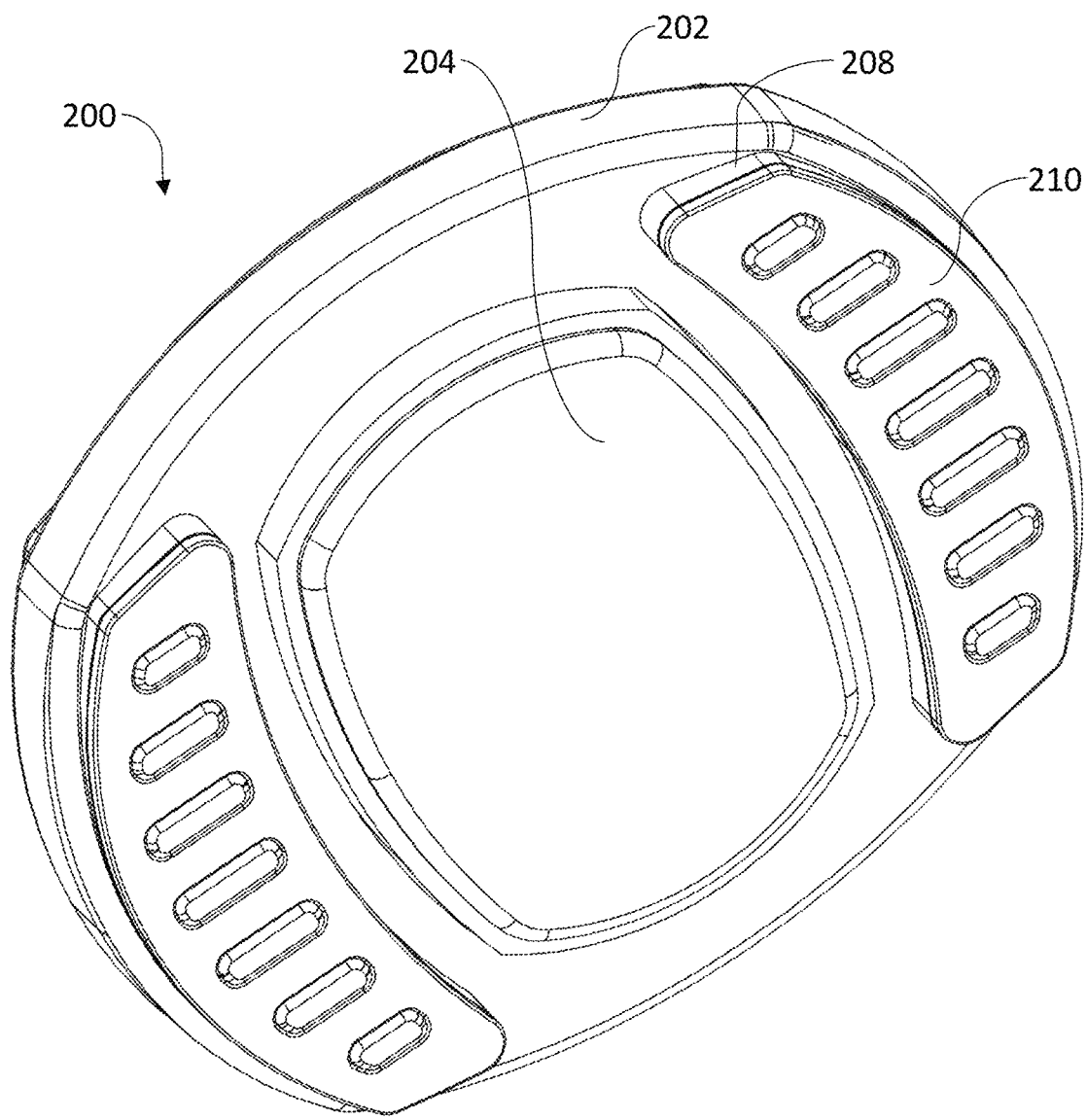
FIG. 9 illustrates a bottom perspective view of a pain-relieving apparatus.
Figure 10:
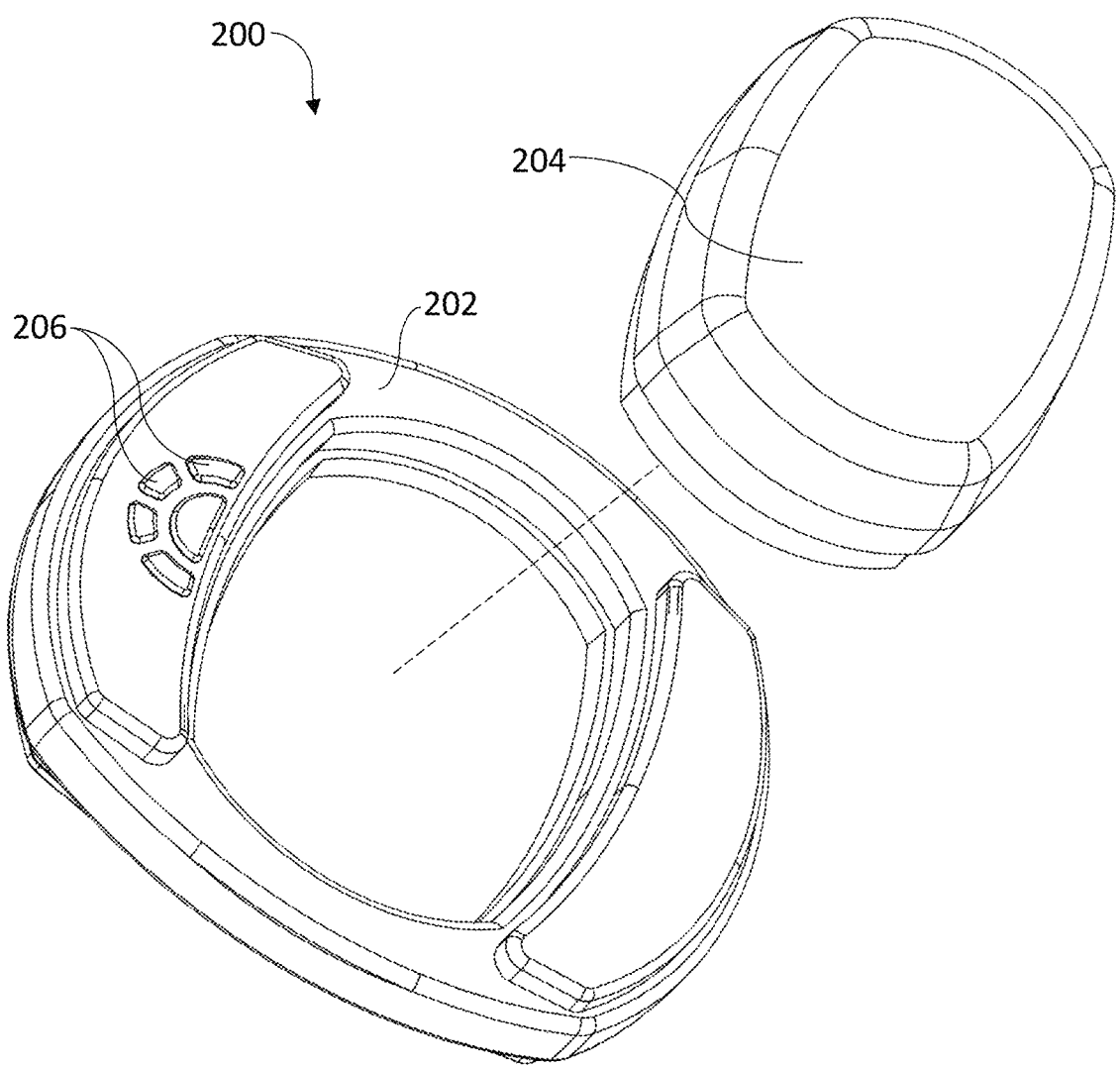
FIG. 10 illustrates a top perspective view of a pain-relieving apparatus with a removably attachable cooling component decoupled therefrom.
Figure 11:
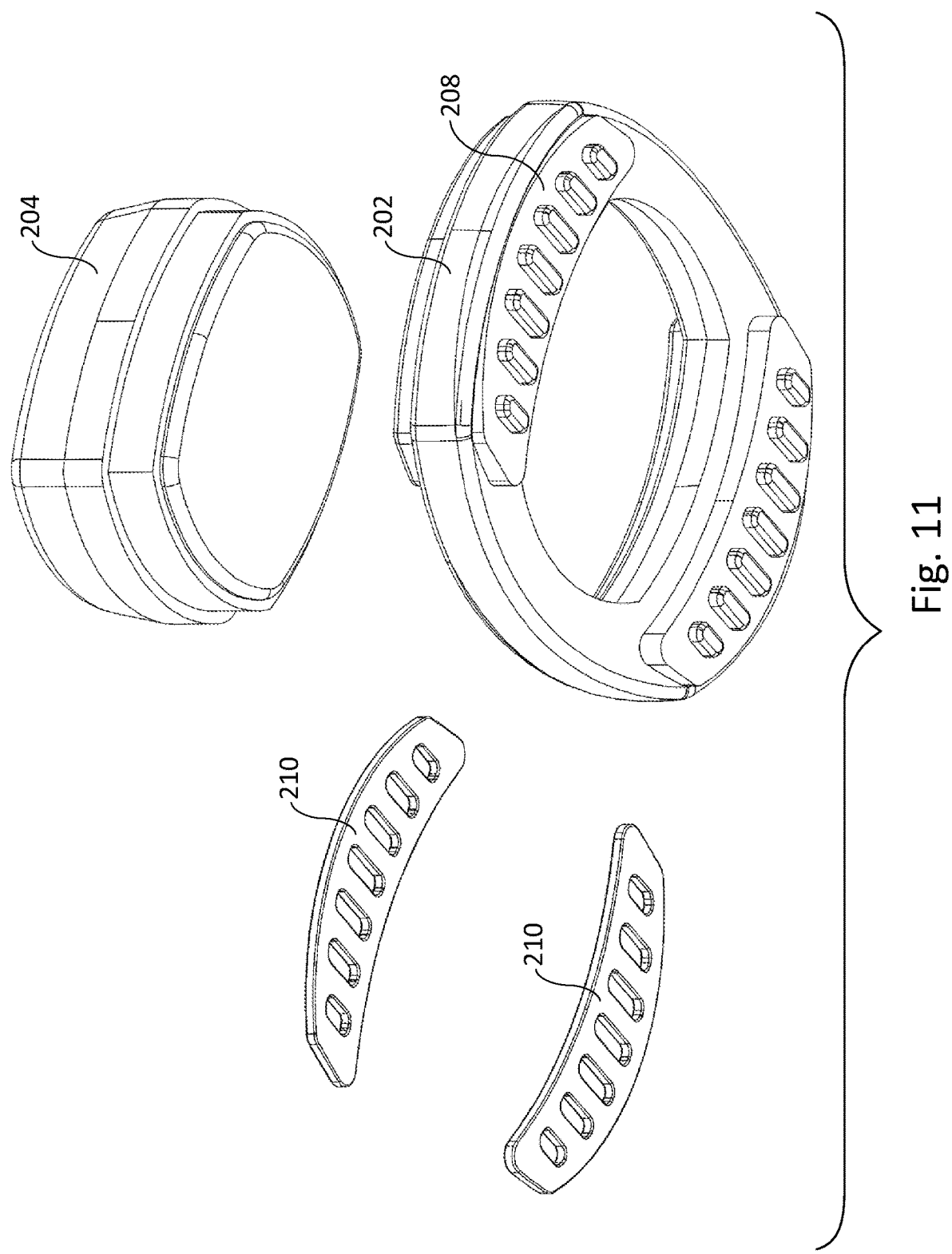
FIG. 11 illustrates an exploded view of a pain-relieving apparatus.

In one embodiment, as shown in FIGS. 6-7, a pain-relieving apparatus 100 comprises a wireless transceiver that allows it to connect wirelessly to a smartphone or tablet. For example, WiFi® or Bluetooth® connections may be used. The user may then control (i.e., turn modalities on/off and vary intensity) the pain-relieving apparatus 100 via application software on the phone 124 or tablet. In one embodiment, the phone application may also track the different types of pain modalities used as well as their intensity so that a user may have a record of the different approaches and know which approach was successful in either eliminating or decreasing the pain.

In one embodiment, a method of using the pain-relieving apparatus 100 comprises a user placing the pain-relieving apparatus 100 on a painful area of the body and either holding the pain-relieving apparatus in place or securing it via attachment sites 122A, 122B. Through user inputs 106 or via the smartphone 124, the user selects which type of pain control modality to use. The user adjusts whether the pain control modalities are on or off and the intensity of each modality through the user inputs 106 or the software application on the phone or tablet. The user finds the pain control modalities that treat his/her pain best. For example, the user may select a plate 116 and vacuum apertures 112 to provide heat/cold and suction, respectively. The user then determines if the pain control modalities distract the pain stimulus and provide relief. If the modalities do not provide relief, then the user selects other modalities to use, alone or together at various intensities, to determine the best pain relief option.

As shown in FIGS. 8-11, in one embodiment, a pain-relieving apparatus 200 comprises a housing 202, a removably attachable cooling component 204, user inputs 206, and medicinal holders 208. In an alternate embodiment, the removably attachable cooling component 204 may heat as well as cool. The medicinal holders 208, located on the housing 202, may receive any local anesthetics, such as lidocaine patches 210. The lidocaine patches 210, for example, may be releasably adhered to the medicinal holders 208. Further, the housing 202 may vibrate as a whole to provide an additional pain control modality to those mentioned above. It will be appreciated that the pain-relieving apparatus 200, in one embodiment, may further comprise vibration stimulators (e.g., vibrating protrusions). In an alternate embodiment, the pain-relieving apparatus 200 may be a single unit with all the components together in one.

Figure 12:
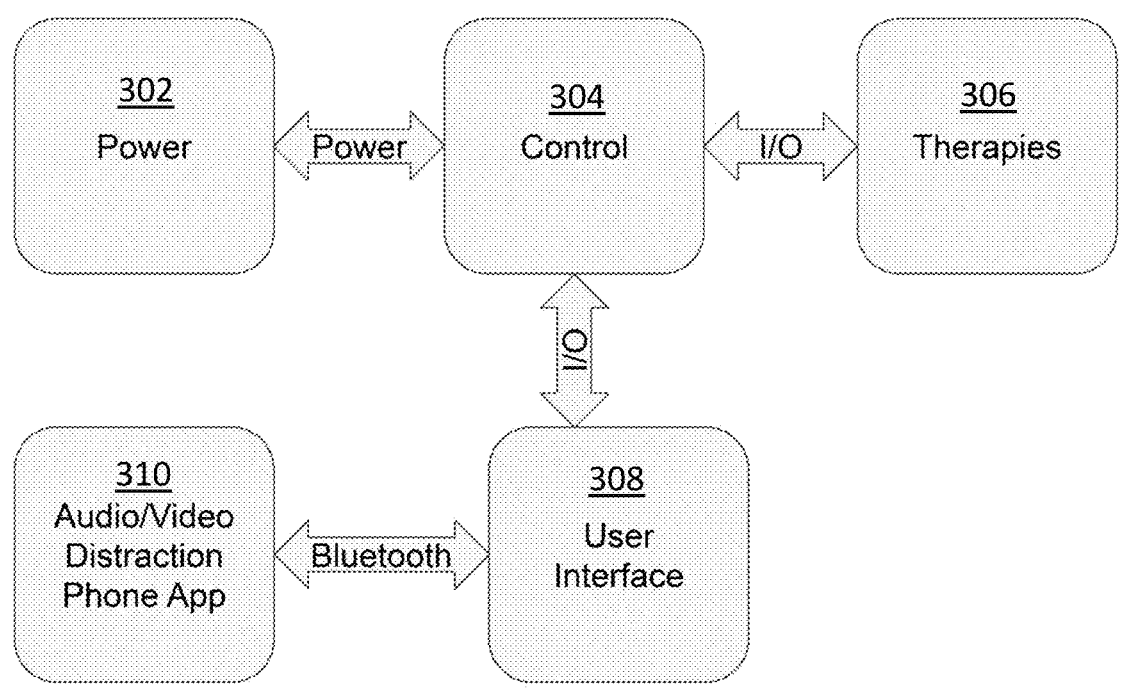
FIG. 12 illustrates a block diagram of a pain-relieving apparatus.
Figure 13:
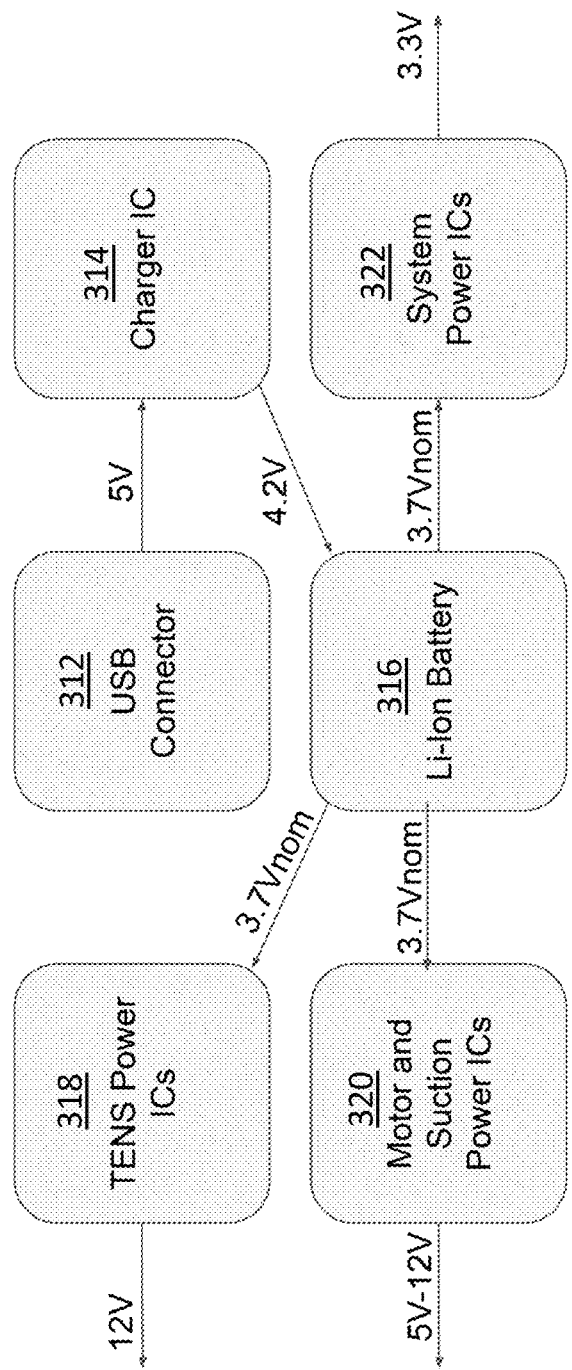
FIG. 13 illustrates a diagram of a power system of a pain-relieving apparatus.

As shown in the pain-relieving apparatus diagram in FIG. 12, power 302 is directed toward control 304 (e.g., microcontroller or other processor). The control 304 can perform I/O (input/output) with therapies 306 (e.g., pain control modalities found on the stimulating surface 104). Further, the control 304 can perform I/O to the user interface 308. The user interface 308 may interact with an audio/video distraction phone app 310 via Bluetooth® or WiFi®. Referring to a power diagram in FIG. 13, a USB connector 312, which may provide a 5V power supply, supplies power to a charger integrated circuit ("IC") 314 that sends 4.2 V to a lithium-ion battery 316. The lithium-ion battery 316 provides power to various features of the pain-relieving apparatus 100. In particular, the lithium-ion battery 316 supplies a TENS power ICs 318 with 3.7 Vnom (battery's nominal voltage). The TENS power ICs 318 may then release 12V. The lithium-ion battery 316 also supplies 3.7 Vnom to motor and suction power ICs 320. The motor and suction power ICs 320 may then produce 5V-12V. Lastly, the lithium-ion battery 316 may supply 3.7 Vnom to System Power ICs 322. The system power ICs 322 may then produce 3.3V.

Figure 14:
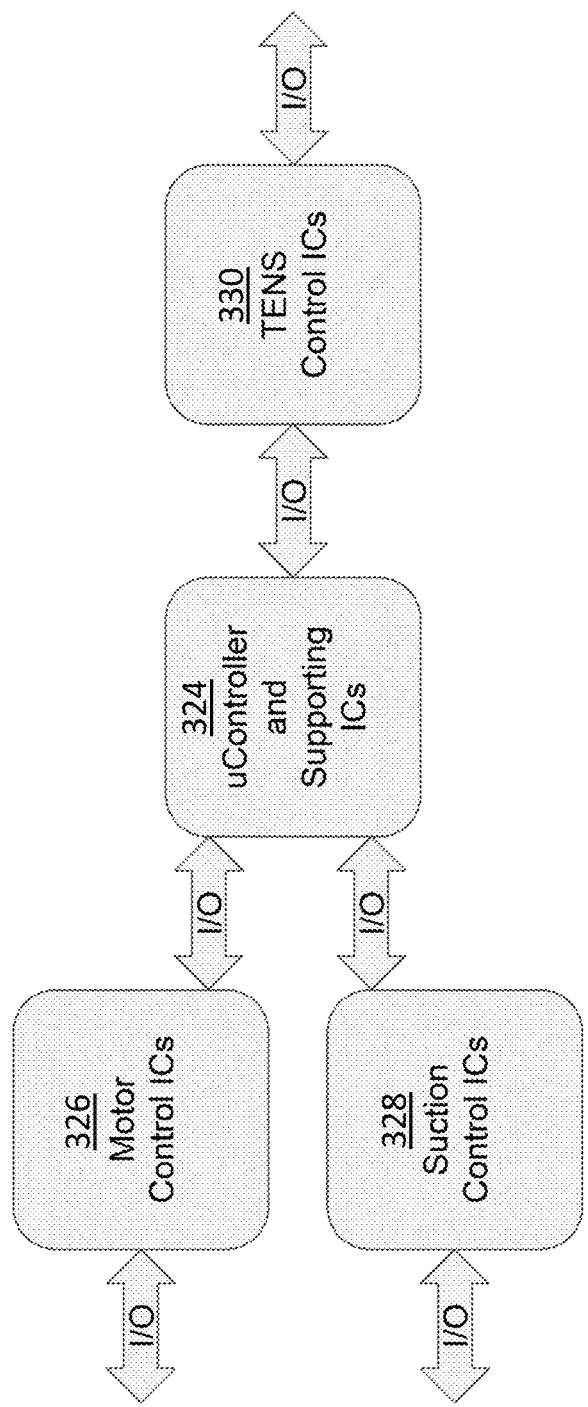
FIG. 14 illustrates a diagram of a control system of a pain-relieving apparatus.

Further, as shown in a control diagram in FIG. 14, I/O may be performed via a microcontroller and supporting ICs 324. The microcontroller and supporting ICs 324 can then perform I/O with motor control ICs 326, suction control ICs 328, and TENS control ICs 330. The TENS, motor, and suction control ICs 326-330 can also perform its own I/O.

Figure 15:
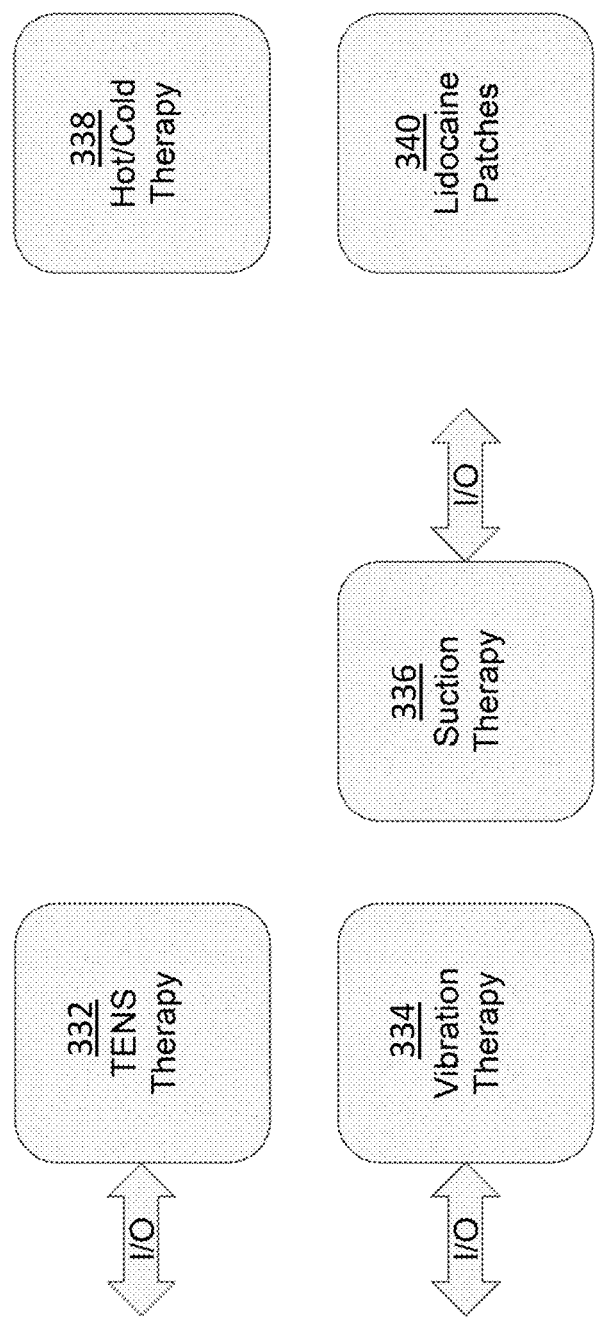
FIG. 15 illustrates a diagram of a set of therapies of a pain-relieving apparatus.
Figure 16:
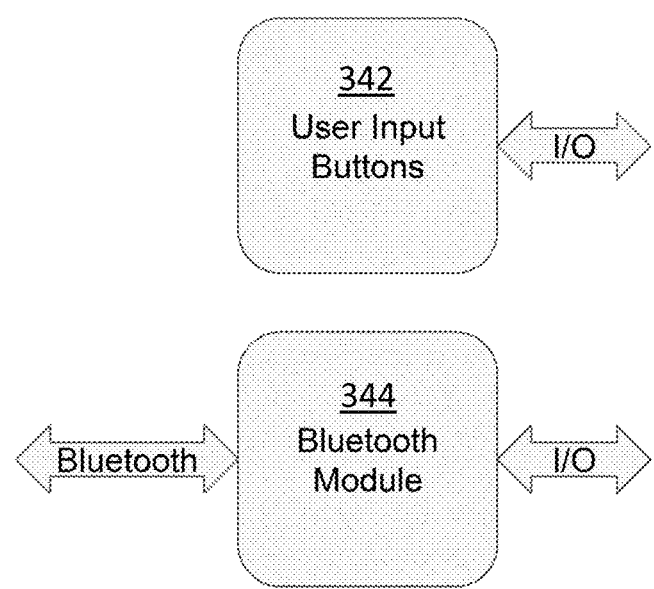
FIG. 16 illustrates a diagram of a user interface of a pain-relieving apparatus.

Therapies, used interchangeably with "pain-control modalities," can control I/O. For example, as shown in FIG. 15, I/O can be performed for TENS therapy 332, vibration therapy 334, and suction therapy 336, while hot/cold therapy 338 and lidocaine patches 340 do not have I/O. In an alternative embodiment, hot/cold therapy 338 may have I/O capabilities. In FIG. 16, the user interface is shown. In particular, user input buttons 342 can perform I/O and a Bluetooth module 344 can perform I/O and may also receive and/or transmit communication via Bluetooth®.

The pain-relieving apparatus 100, 200 comprises multiple stimuli to decrease and eliminate pain using, for example, vibration, cooling, heating, suction, TENS (transcutaneous electrical nerve stimulation), lidocaine, and sound to overload the nerve pathways in a unique combinatorial way to decrease and/or eliminate the pain signals traveling to the brain. This allows a user to select specific modalities of pain control so that a person can use one, some, or all of the above modalities to control pain in a non-narcotic or addictive manner. Because all of the modalities are combined into a single apparatus, it is convenient, less expensive, and more effective for a user. As a result, dependence on medication may decrease.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. A pain-relieving apparatus, comprising:
   a housing comprising:
      a TENS output connector;
      at least one attachment site for coupling the housing to a user;
      a stimulating surface for interrupting a user's pain signals to the brain, the stimulating surface comprising:
         a suction ring comprising a plurality of vacuum apertures therein, at least one vibration stimulator,
         a removably attachable heating or cooling plate positioned within the suction ring and surrounded by the plurality of vacuum apertures,
         a plurality of lidocaine patches,
         a sound speaker;
      a wireless transceiver configured to wirelessly couple to a smartphone;
      a battery charging port; and
      a smartphone software application configured to wirelessly couple the smartphone to the wireless transceiver, the smartphone software application configured further to allow the user to control an activity and intensity of the plurality of vacuum apertures, the at least one vibration stimulator, and the sound speaker.

2. The pain-relieving apparatus of claim 1, wherein the suction ring is an elastomer material.

3. The pain-relieving apparatus of claim 1, wherein the plurality of vacuum apertures are evenly spaced in a circular formation within the suction ring.

4. The pain-relieving apparatus of claim 1, wherein the plurality of lidocaine patches are removably attachable.

* * * * *